United States Patent
Jeon et al.

(10) Patent No.: US 9,814,749 B2
(45) Date of Patent: Nov. 14, 2017

(54) COMPOSITION FOR PREVENTING OR TREATING DEMENTIA CONTAINING PRUNUS MUME EXTRACT

(75) Inventors: Won Kyung Jeon, Seoul (KR); Jung-Soo Han, Seoul (KR); Chang Hyun Han, Daejeon (KR); Goya Choi, Daejeon (KR)

(73) Assignee: Korea Institute of Oriental Medicine, Daejeon (KR)

( * ) Notice: Subject to any disclaimer, the term of this patent is extended or adjusted under 35 U.S.C. 154(b) by 563 days.

(21) Appl. No.: 13/996,319

(22) PCT Filed: Oct. 4, 2011

(86) PCT No.: PCT/KR2011/007314
§ 371 (c)(1),
(2), (4) Date: Aug. 6, 2013

(87) PCT Pub. No.: WO2012/046993
PCT Pub. Date: Apr. 12, 2012

(65) Prior Publication Data
US 2013/0309334 A1 Nov. 21, 2013

(30) Foreign Application Priority Data

Oct. 4, 2010 (KR) .................. 10-2010-0096417
Oct. 4, 2011 (KR) .................. 10-2011-0100670

(51) Int. Cl.
*A61K 36/736* (2006.01)
(52) U.S. Cl.
CPC ........ *A61K 36/736* (2013.01); *A61K 2236/33* (2013.01)
(58) Field of Classification Search
None
See application file for complete search history.

(56) References Cited

U.S. PATENT DOCUMENTS

| 7,799,763 B2 | 9/2010 | Okada et al. |
| 2004/0002423 A1 | 1/2004 | Ohnogi et al. |
| 2005/0031711 A1* | 2/2005 | Park ............ A61K 36/185 424/728 |
| 2006/0257351 A1 | 11/2006 | Chiba |

FOREIGN PATENT DOCUMENTS

| CN | 1183469 A | 6/1998 |
| CN | 1218107 A | 6/1999 |
| CN | 101596246 A | 12/2009 |
| CN | 101732301 A | 6/2010 |
| KR | 10-2005-0035906 A | 4/2005 |
| KR | 20050035906 A * | 4/2005 |

OTHER PUBLICATIONS

Hempen et al. "A Materia Medica for Chinese Medicine: Plants, Minerals, and Animal Products". Elsevier: Munchin (2009). p. 996.*

* cited by examiner

*Primary Examiner* — Amy L Clark
(74) *Attorney, Agent, or Firm* — Norton Rose Fulbright US LLP

(57) ABSTRACT

The present invention relates to a composition for preventing or treating dementia containing an extract of *Prunus mume* (Fructus Mume), and the *Prunus mume* extract of the present invention has outstanding effects in improving spatial recognition ability and in normalizing hippocampal damage (normalizing ERK phosphorylation, increasing ChAT and normalizing NF-kappa B) induced by chronic vascular brain damage in a vascular dementia animal model, and hence can be used to advantage as a medicinal product for preventing or treating dementia diseases and as a functional health food for preventing or alleviating dementia diseases that accompany vascular brain damage such as vascular dementia.

4 Claims, 10 Drawing Sheets

COMPOSITION FOR PREVENTING OR TREATING DEMENTIA CONTAINING PRUNUS MUME EXTRACT

CROSS-REFERENCE TO RELATED APPLICATIONS

This application is a 371 of PCT/KR2011/007314, filed on Oct. 4, 2011, which claims the benefit of Korean Patent Application Nos. 10-2010-0096417, filed on Oct. 4, 2010 and 10-2011-0100670, filed on Oct. 4, 2011, the contents of each of which are incorporated herein by reference.

BACKGROUND OF THE INVENTION

1. Field of the Invention

The present invention relates to a composition for preventing or treating dementia containing Fructus Mume extract.

2. Description of the Related Art

Dementia is diagnosed when memory disorder is so severe as to bring difficulty in daily life including work, social life, and personal relationship with accompanying at least one of the following 4 symptoms; speech disorder, disorientation, decline of calculation ability, and character & emotional changes. Dementia is a pathological symptom which should be distinguished from normal aging. Dementia is divided into Alzheimer's disease, vascular dementia, and other dementias caused by alcoholism, trauma and sequela of Parkinson's disease, according to the cause. Vascular dementia is generally caused by cerebral infraction or stroke, which causes memory loss due to the brain cell damage around the onset region. In the meantime, Alzheimer's disease is a kind of degenerative brain diseases caused by brain cell destruction. In the early stage of Alzheimer's disease, such symptoms as hypomnesia, character change, and decline of thinking ability are shown and the progress is slow. However, most of Alzheimer's patients die of pneumonia in 8-10 years from the onset of the disease. According to the recent epidemiological studies, the risk factors for the cerebrovascular diseases including hypertension, diabetes, hyperlipidemia, and heart disease can increase the incidence rate of not only vascular dementia but also Alzheimer's disease. However, the exact cause or treatment method of dementia has not been developed, yet.

The therapeutic agents for dementia are classified according to the lesion and cause of the disease, which are exemplified by acetylcholine esterase inhibitors, antioxidants, anti-inflammatory agents, hormone formulations, cholesterol lowering agents, and β-amyloid blockers, etc. The said acetylcholine esterase increases the activity of cholinergic neurotransmitter system remaining undestroyed so as to recover the damaged cognitive function even it partially.

Dementia patients are estimated approximately 400,000 in 2008. Owing to rapid aging, it seems that the number of dementia patients will be increased to 461,000 in 2010 and 693,000 in 2020. As the population of dementia patients grows, the domestic market for dementia drugs makes rapid increasing curve and the volume is already as big as over 130 billion Korean Won.

Fructus Mume is a medicinal ingredient prepared by the following processes: unripe fruits of *Prunus mume* are placed in a pot and then closed with a lid; and the pot is completely sealed with mud, which is heated until the fruits turn black. Fructus Mume is effective in eliminating old chronic cough and phlegm and in quenching thirst and in relieving the feeling of pressure in chest and digestion as well. In addition, Fructus Mume is known to have immune enhancing activity, anti-bacterial activity, and hypoglycemic effect. There are some studies to disclose the effect of Fructus Mume: Pharmacentical extracts from Mume Fructus effective for the inhibition of urease activity of *Helicobacter pylori* epithelial cells of stomach (Korean Patent Publication No. 2006-0040254), Analgesic activity of sitosterol-O-D-glucose isolated from Mume Fructus extract (Korean Patent Publication No. 1998-0043925), and Composition for enhancing blood circulation containing the extract or fraction of *Prunus Mume* as an active ingredient (Korean Patent Publication No. 2010-0042414). Another report says that modified SAGUNZA-TANG comprising the extracts of Maesil (*Prunus mume*), *Polygonatum odoratum*, Galgeun (*Pueraria radix*), and Cinnamomi cortex is effective in preventing and treating dementia (Pharmaceutical composition containing the modified SAGUNZA-TANG which is effective in improvement of anti-stress and brain function, Korean Patent Publication No. 2005-0035906). It is known that the Maesil (*Prunus mume*) extract in the said modified SAGUNZA-TANG is responsible for the acceleration of digestion and carbohydrate metabolism to make energy (glucose) supply to brain smooth to increase brain activity. The Maesil (*Prunus mume*) extract therein also plays a role in enhancing taste and flavor with its unique sour taste. However, there is no evidence that Maesil (*Prunus mume*) extract is effective in preventing and treating dementia. Studies have not been made on the hippocampal damage recovery activity of Fructus Mume extract processed from Maesil (*Prunus mume*).

Therefore, the present inventors studied on the effect of Fructus Mume extract and accordingly confirmed that the Fructus Mume extract was effective in improving spatial recognition ability and in normalizing hippocampal damage in a vascular dementia animal model, leading to the completion of this invention by further confirming that the Fructus Mume extract could be effectively used as an active ingredient for a composition for preventing or treating dementia.

SUMMARY OF THE INVENTION

It is an object of the present invention to provide a pharmaceutical composition for preventing or treating dementia comprising Fructus Mume extract as an active ingredient.

It is another object of the present invention to provide a functional health food composition for preventing or alleviating dementia comprising Fructus Mume extract as an active ingredient.

To achieve the above objects, the present invention provides a pharmaceutical composition for preventing or treating dementia comprising Fructus Mume extract as an active ingredient.

The present invention also provides a functional health food composition for preventing or alleviating dementia comprising Fructus Mume extract as an active ingredient.

The present invention further provides a method for the treatment of dementia containing the step of administering a pharmaceutically effective dose of Fructus Mume extract to a subject having dementia.

The present invention also provides a method for the prevention of dementia containing the step of administering a pharmaceutically effective dose of Fructus Mume extract to a subject.

The present invention also provides a use of Fructus Mume extract for the preparation of a medicinal drug for preventing or treating dementia.

In addition, the present invention provides a use of Fructus Mume extract for the preparation of a functional health food for preventing or alleviating dementia.

Advantageous Effect

As explained hereinbefore, the Fructus Mume extract of the present invention has excellent effect in improving spatial recognition ability and in normalizing hippocampal damage (normalizing ERK phosphorylation, increasing ChAT and normalizing NF-kappa B) induced by chronic vascular brain damage in a vascular dementia animal model, so that it can be effectively used for the prevention or treatment of such disease accompanied by vascular brain damage including vascular dementia.

BRIEF DESCRIPTION OF THE DRAWINGS

The application of the preferred embodiments of the present invention is best understood with reference to the accompanying drawings, wherein.

SHAM+Vehicle; vehicle treated group
$BCCA_o$+Vehicle; brain damaged group
$BCCA_o$+Choto-san 300; brain damaged group treated with 300 mg/kg of Choto-san
$BCCA_o$+F. Mume 100; brain damaged group treated with 100 mg/kg of F. Mume
$BCCA_o$+F. Mume 200; brain damaged group treated with 200 mg/kg of F. Mume
$BCCA_o$+F. Mume 400; brain damaged group treated with 400 mg/kg of F. Mume

SHAM+Vehicle; vehicle treated group
$BCCA_o$+Vehicle; brain damaged group
$BCCA_o$+Choto-san 300; brain damaged group treated with 300 mg/kg of Choto-san
$BCCA_o$+F. Mume 100; brain damaged group treated with 100 mg/kg of F. Mume
$BCCA_o$+F. Mume 200; brain damaged group treated with 200 mg/kg of F. Mume
$BCCA_o$+F. Mume 400; brain damaged group treated with 400 mg/kg of F. Mume

SHAM+Vehicle; vehicle treated group
$BCCA_o$+Vehicle; brain damaged group
$BCCA_o$+Choto-san 300; brain damaged group treated with 300 mg/kg of Choto-san
$BCCA_o$+F. Mume 100; brain damaged group treated with 100 mg/kg of F. Mume
$BCCA_o$+F. Mume 200; brain damaged group treated with 200 mg/kg of F. Mume
$BCCA_o$+F. Mume 400; brain damaged group treated with 400 mg/kg of F. Mume

SHAM+Vehicle; vehicle treated group
$BCCA_o$+Vehicle; brain damaged group
$BCCA_o$+Choto-san 300; brain damaged group treated with 300 mg/kg of Choto-san
$BCCA_o$+F. Mume 100; brain damaged group treated with 100 mg/kg of F. Mume
$BCCA_o$+F. Mume 200; brain damaged group treated with 200 mg/kg of F. Mume
$BCCA_o$+F. Mume 400; brain damaged group treated with 400 mg/kg of F. Mume

SHAM+Vehicle; vehicle treated group
$BCCA_o$+Vehicle; brain damaged group
$BCCA_o$+Choto-san 300; brain damaged group treated with 300 mg/kg of Choto-san
$BCCA_o$+F. Mume 200; brain damaged group treated with 200 mg/kg of F. Mume

CA 1; Cornus Ammonis 1
CA 3; Cornus Ammonis 3
DG; dentate gyrus
SHAM+Vehicle; vehicle treated group
$BCCA_o$+Vehicle; brain damaged group
$BCCA_o$+Choto-san 300; brain damaged group treated with 300 mg/kg of Choto-san
$BCCA_o$+F. Mume 200; brain damaged group treated with 200 mg/kg of F. Mume

Figure 1:
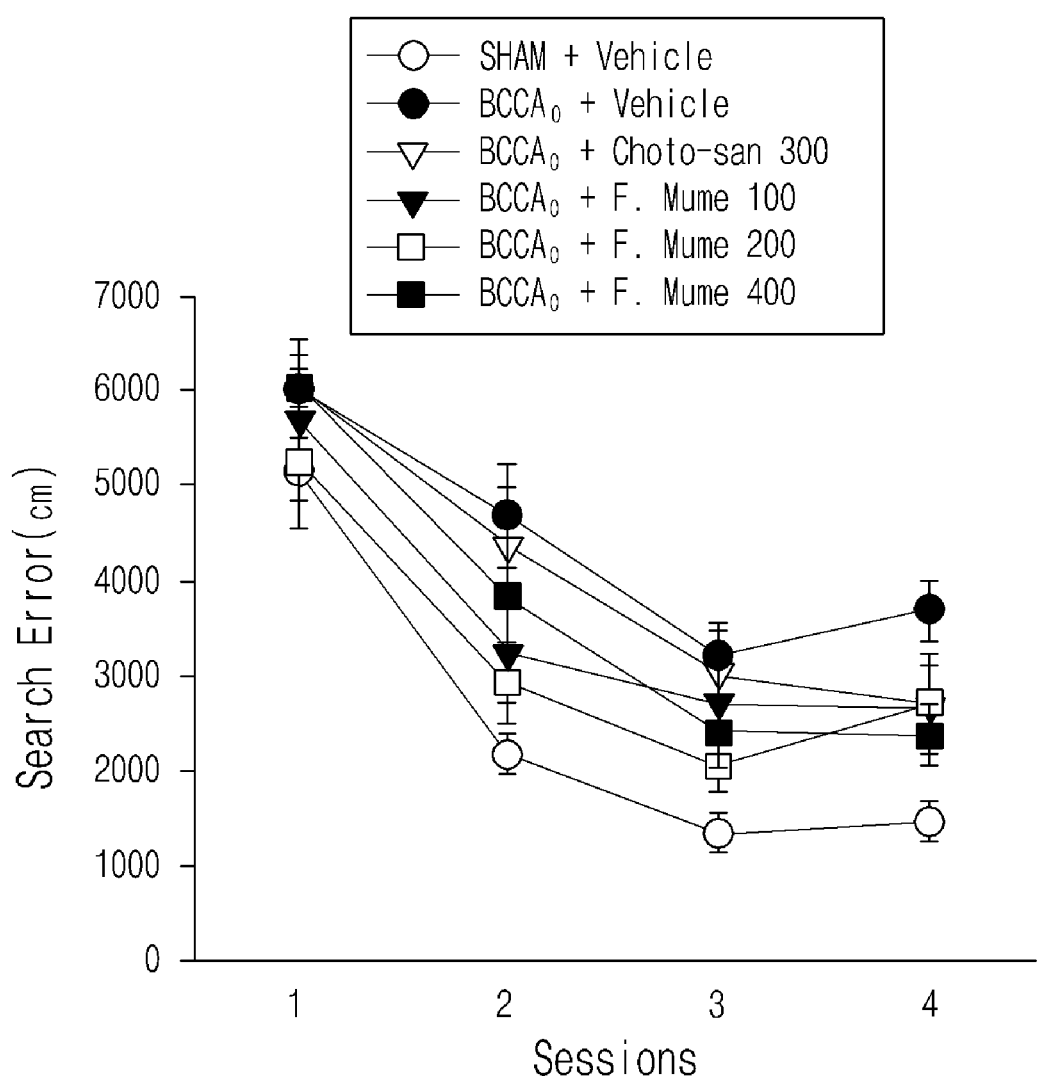
FIG. 1 is a graph illustrating search error over trail sessions, showing the effect of the Fructus Mume extract of the present invention on the normalization of spatial recognition ability.

SHAM+Vehicle; vehicle treated group
$BCCA_o$+Vehicle; brain damaged group
$BCCA_o$+Choto-san 300; brain damaged group treated with 300 mg/kg of Choto-san
$BCCA_o$+F. Mume 100; brain damaged group treated with 100 mg/kg of F. Mume
$BCCA_o$+F. Mume 200; brain damaged group treated with 200 mg/kg of F. Mume
$BCCA_o$+F. Mume 400; brain damaged group treated with 400 mg/kg of F. Mume

DESCRIPTION OF THE PREFERRED EMBODIMENTS

Hereinafter, the present invention is described in detail.

The present invention provides a pharmaceutical composition for preventing or treating dementia comprising Fructus Mume extract as an active ingredient.

The Fructus Mume extract of the present invention is preferably prepared by the following steps:

1) extracting Fructus Mume by using water, alcohol, or the mixture thereof; and 2) obtaining dried powder by concentrating the extract of step 1) under the reduced pressure and drying thereof, but not always limited thereto.

In the above method, the Fructus Mume of step 1) was unripe fruit of *Prunus mume* that was placed in a pot and covered with a lid, followed by sealing with mud and heating until the fruit turned black. The fruit could be obtained from the cultivation or purchased on the market.

In the above method, the said water of step 1) is distilled water. When alcohol is used, $C_1$-$C_4$ lower alcohol is preferred. At this time, the lower alcohol herein is ethanol or methanol. Organic materials are well eluted in 100% alcohol and glycosides are better eluted in alcohol aqueous solution. So, either alcohol or alcohol aqueous solution can be used. A solvent for the extraction is preferably added at the volume of 2-10 times the volume of Fructus Mume, and more preferably at the volume of 3~4 times the volume of Fructus Mume, but not always limited thereto. The extraction method is one of the conventional methods accepted in this field, which is exemplified by hot-water extraction, enfleurage, reflux extraction, filtration and ultrasonification extraction. Herein, ultrasonification extraction or hot-water extraction is preferred and ultrasonification/heat combined extraction is more preferred, but not always limited thereto. The temperature of the solvent for the extraction is preferably 20° C.-100° C., and more preferably 95° C., but not always limited thereto. The extraction time is preferably 1-24 hours and more preferably 2 hours, but not always limited thereto. The extraction is preferably repeated 1-5 times and more preferably repeated 3 times, but not always limited thereto.

In the above method, the concentration under the reduced pressure and drying of step 2) can be performed according to the conventional method used in this field.

The said dementia is preferably vascular dementia or Alzheimer's disease, and more preferably vascular dementia, but not always limited thereto.

In a preferred embodiment of the present invention, the dried Fructus Mume (2 kg) was placed in the ultrasonification/heat combined extractor (OM30-EP, SONIMEDI), to which 8 l of distilled water was added, followed by extraction at 95° C. for 120 minutes. The extracted solution was dried in Exdryer (SONIMEDI) to give Fructus Mume extract (yield: 16.225%).

In a preferred embodiment of the invention, the test animal used for the construction of vascular dementia animal model was Wister rat. Chronic cerebral hypoperfusion was induced by bilateral common carotid artery occlusion (2V0, referred as "BCCAo" hereinafter) (Wakita et al., 1994). For the oral administration of the Fructus Mume extract of the present invention to the test animal constructed above, the extract was prepared at different concentrations [low concentration (100 mg/kg), medium concentration (200 mg/kg), and high concentration (400 mg/kg)]. The animal was grouped into 6 groups in total including the control group treated with Chotosan (300 mg/kg), the vehicle treated group, and the experimental groups.

Figure 2:
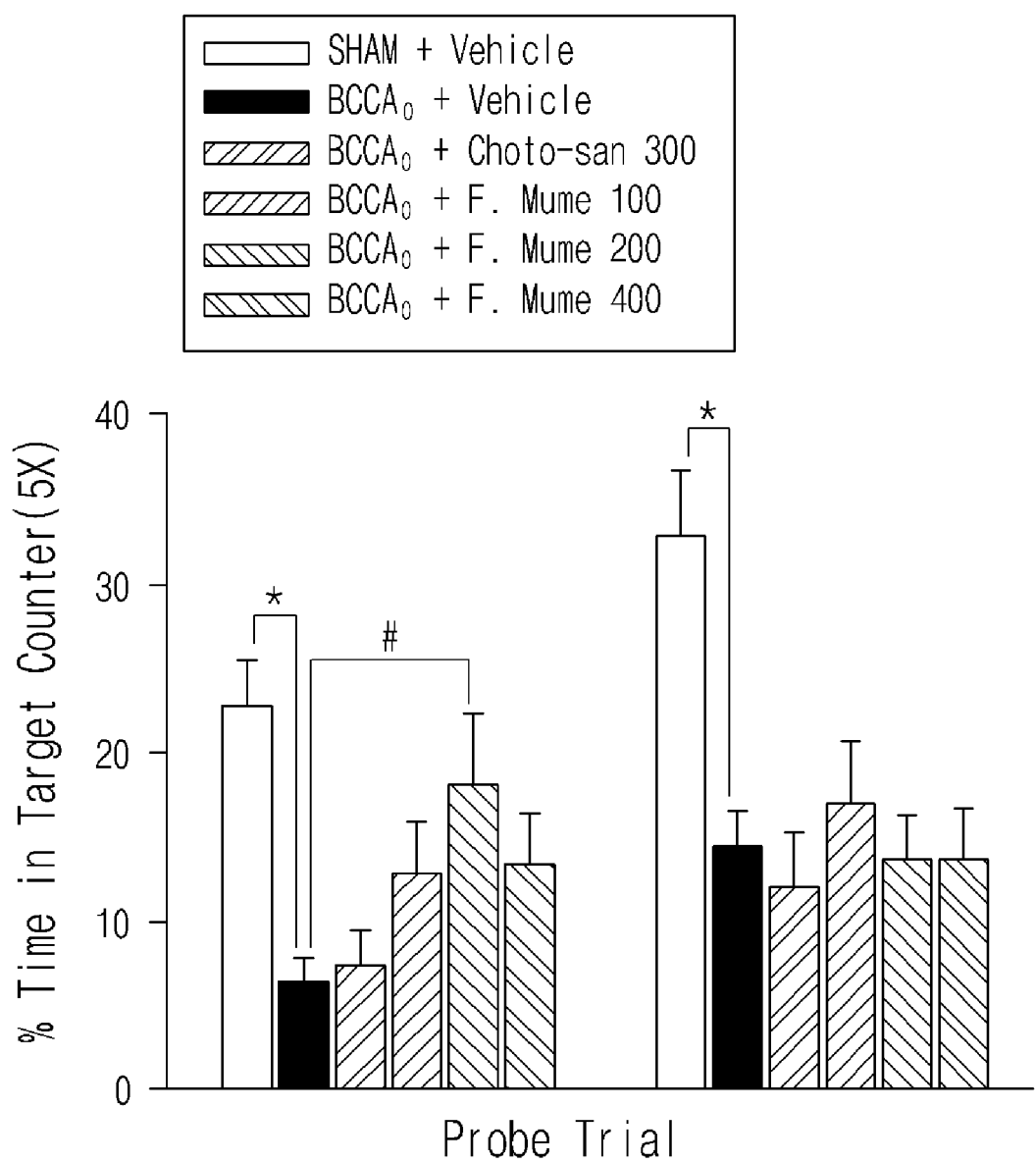
FIG. 2 is a graph illustrating % time in target counter in probe trial, showing the effect of the Fructus Mume extract of the present invention on the normalization of spatial recognition ability.

In a preferred embodiment of the present invention, behavioral analysis was performed with the vascular dementia animal model to investigate the effect of the Fructus Mume extract of the present invention. Particularly, the Fructus Mume extract of the present invention was administered to the vascular dementia animal model for three weeks and training trial (ability to find the marked platform in water maze) was performed. From the result of spatial memory test performed in water maze, it was confirmed that hippocampal dependent learning and memory defects were observed in the Fructus Mume extract treated group, compared with the BCCAo group (FIG. 1). The vehicle treated group animals carried out spatial memory task in water maze well, compared with the BCCAo group animals. In the group treated with 200 mg/kg of the Fructus Mume extract of Example 1, the animals demonstrated as good spatial memory learning ability as the control group. From the result of statistical evaluation, it was confirmed that there was a difference among the groups (F(5,53)=8.26, p=0.000) and as training trail repeated, the speed to find the hidden platform increased (F(3,159)=98.48, p=0.000). To analyze the difference among the groups, post hoc was performed. As a result, compared with the BCCAo group, the animal group treated with 200 mg/kg of the Fructus Mume extract demonstrated excellent spatial memory learning ability (p=0.027). Therefore, the Fructus Mume extract of the present invention was confirmed to be able to normalize spatial memory ability efficiently and be used effectively for the prevention or treatment of dementia. From the results of two probe trails, it was confirmed that the BCCAo group hardly remembered the location of the platform (F(5,53)=7.05, p=0.000), compared with the vehicle treated group (FIG. 2). Probe trials were performed 4 days and 8 days after training. As a result, the animals of the BCCAo group and the group treated with 200 mg/kg of the Fructus Mume extract swam significantly less than the animals of the vehicle treated group in the area 5 times as big as the platform (p=0.014, first probe trial). That result indicated that the Fructus Mume extract of the present invention increased memory ability of the animals.

Figure 4A:
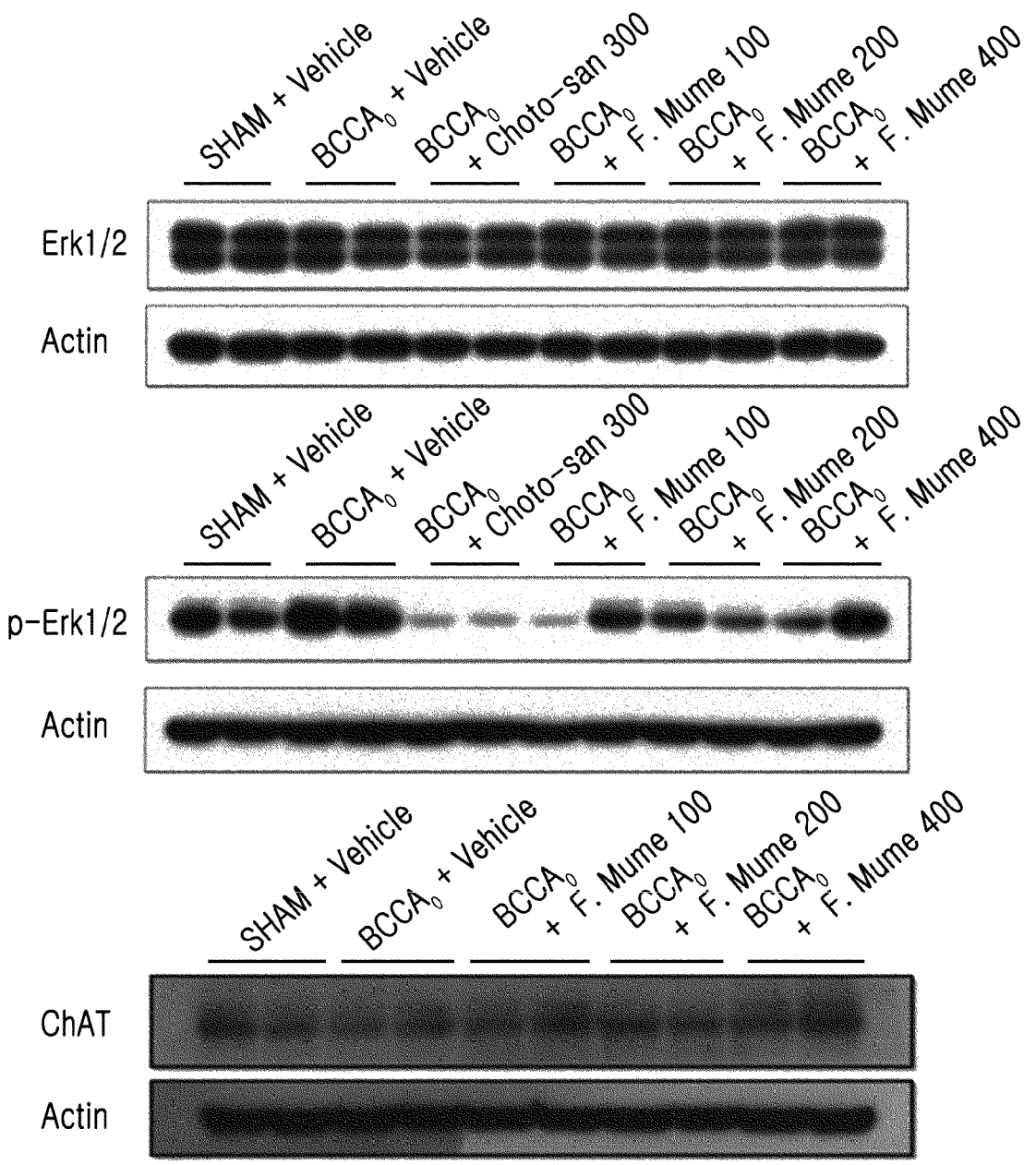
FIG. 4a is a set of photographs illustrating the results of Western blotting and FIG. 4b is a set of graphs illustrating the results of the said Western blotting, showing the effect of the Fructus Mume extract of the present invention on the normalization of hippocampal damage (normalizing ERK (extracellular signal-regulated kinase) phosphorylation and increasing ChAT).
Figure 4B:
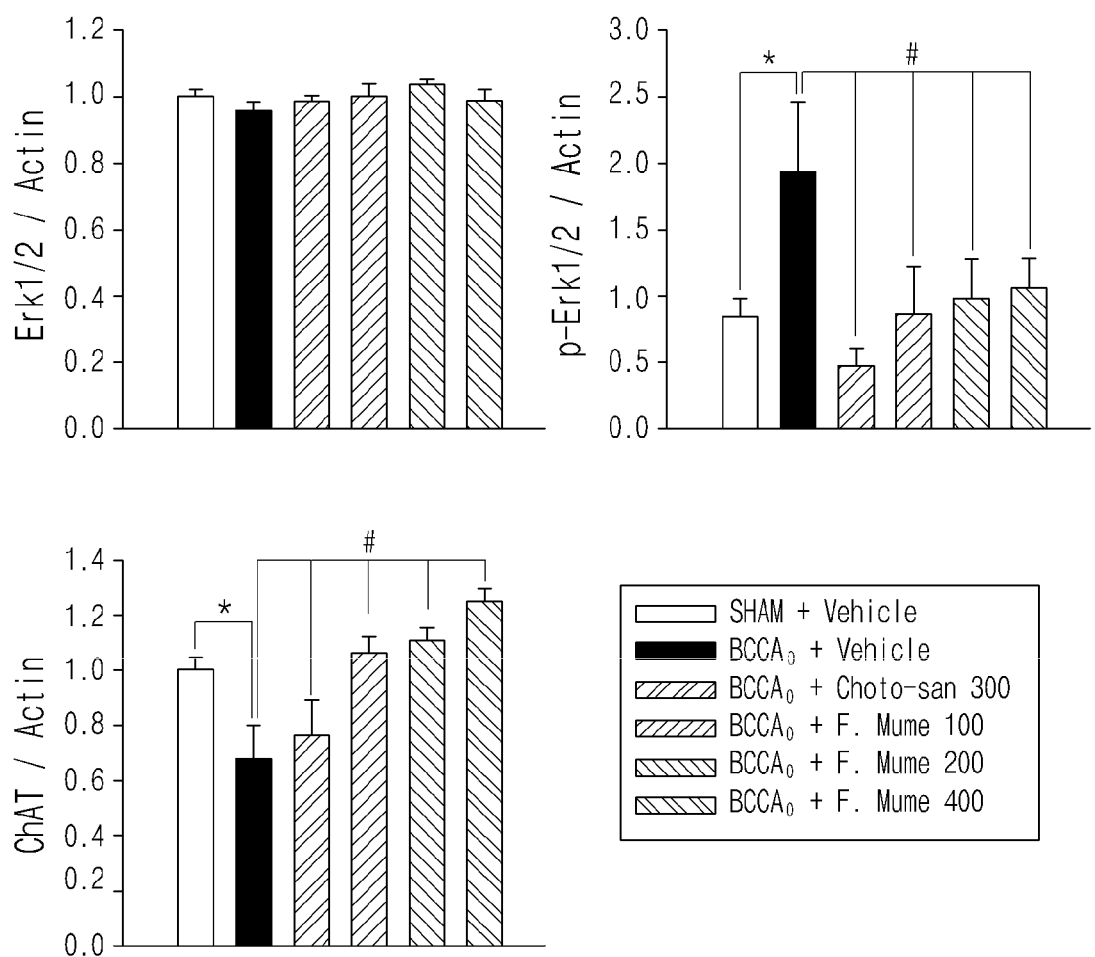
Figure 4C:
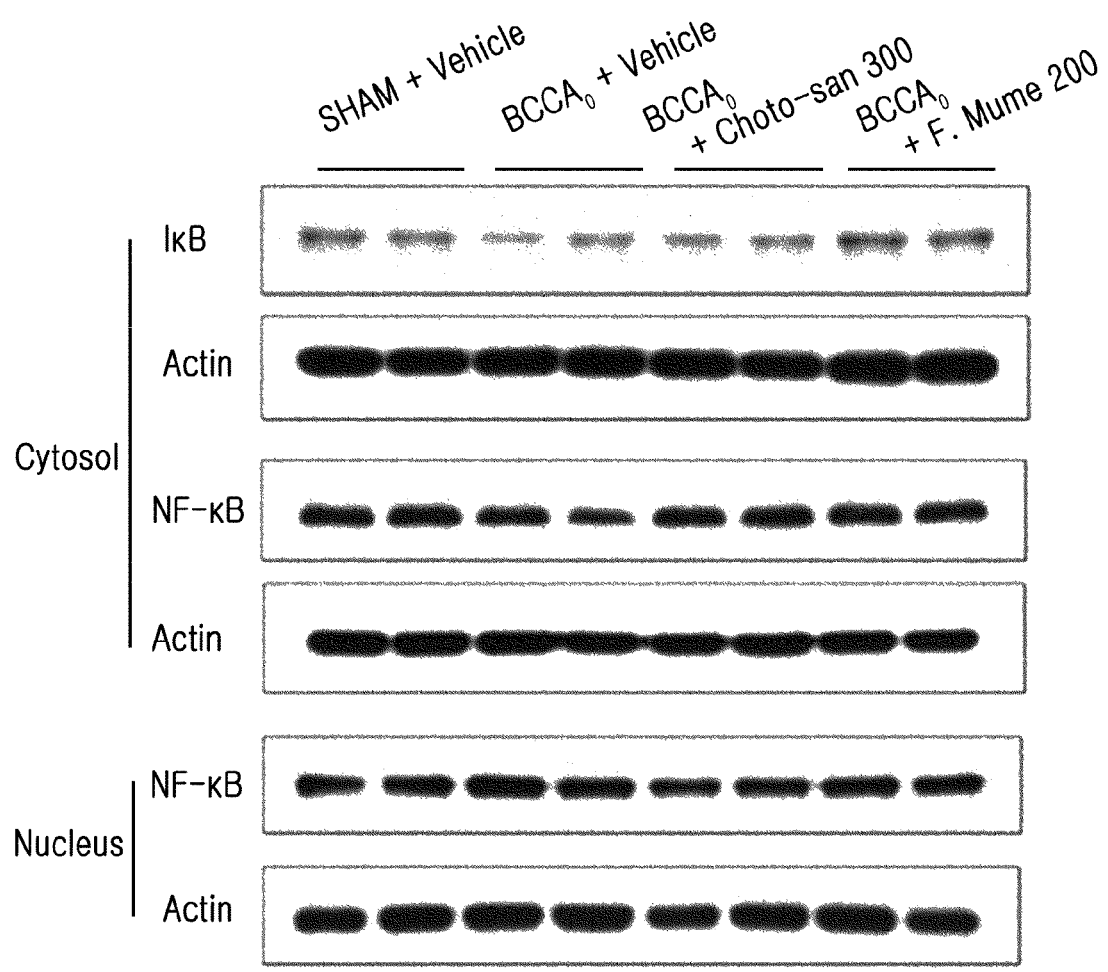
FIG. 4c is a set of photographs illustrating the results of Western blotting and FIG. 4d is a set of graphs illustrating the results of the said Western blotting, showing the effect of the Fructus Mume extract of the present invention on the normalization of hippocampal damage (normalizing NF-kappa B).
Figure 4D:
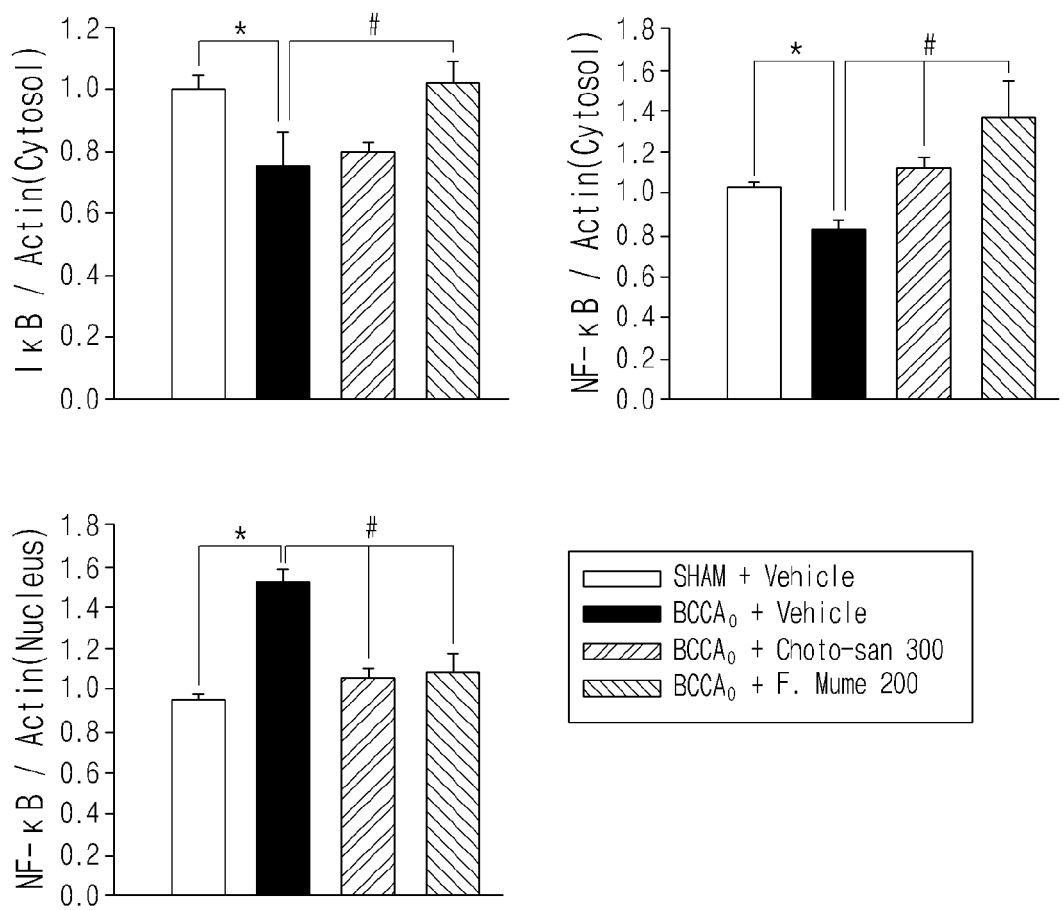

In a preferred embodiment of the present invention, in vivo neurobiological test was performed. FIG. 4a illustrates the result of Western blotting and FIG. 4b is a graph illustrating the result presenting the normalization of hippocampal damage (normalizing ERK phosphorylation and increasing ChAT) by the administration of the Fructus Mume extract of the present invention. FIG. 4c illustrates the result of Western blotting and FIG. 4d is a graph illustrating the result presenting the normalization of hippocampal damage (normalizing NF-kappa B) by the administration of the Fructus Mume extract of the present invention. The BCCAo group animals demonstrated similar ERK level but higher ERK phosphorylation, compared with the vehicle treated group. The treatment of the Fructus Mume extract reduced ERK phosphorylation level significantly (p<0.05). Hippocampal ChAT (choline acetyltransferase, the enzyme used for the generation of acetylcholine) was reduced in the BCCAo group animals, compared with the vehicle treated group, and the reduced ChAT level was normalized by the administration of the Fructus Mume extract. That is, NF-Kappa B level was normalized by the treatment of the Fructus Mume extract.

In a preferred embodiment of the present invention, in vivo histological test was also performed.

Figure 5A:
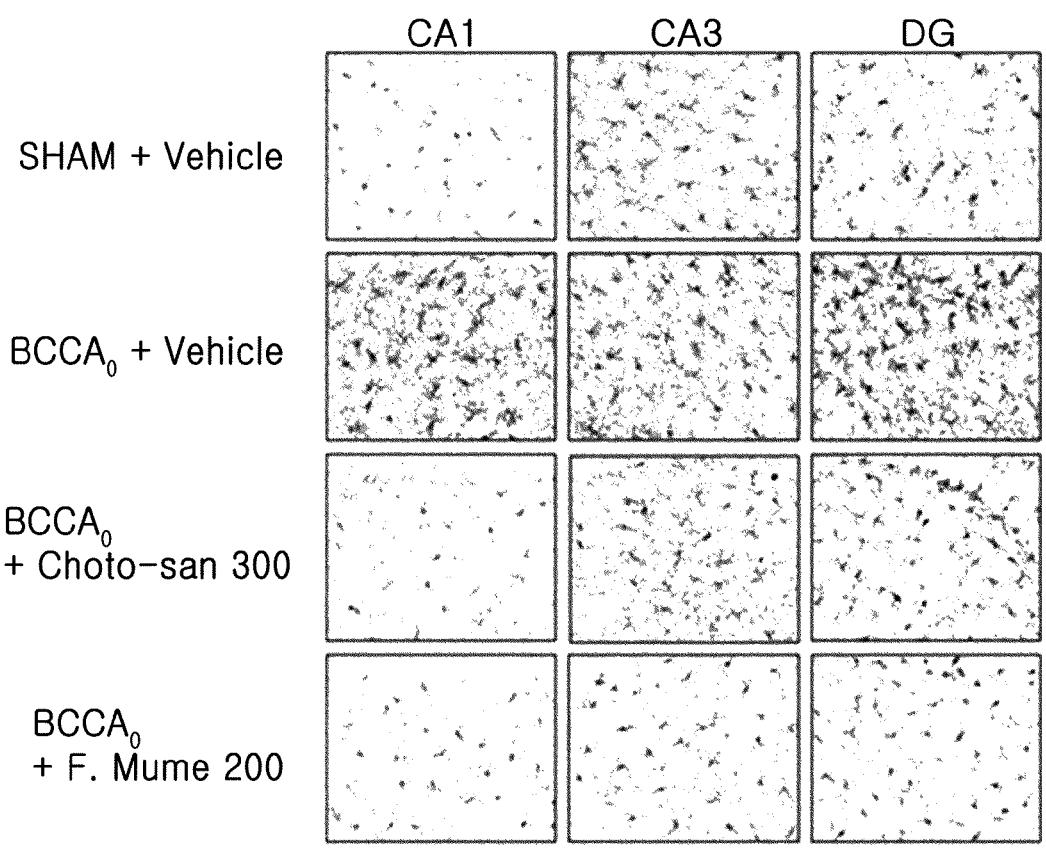
FIG. 5a is a set of photographs illustrating the results of immunohistostaining and FIG. 5b is a graph illustrating the results of the said immunohistostaining, showing the effect of the Fructus Mume extract of the present invention on the normalization of hippocampal damage (suppressing microglial expression).
Figure 5B:
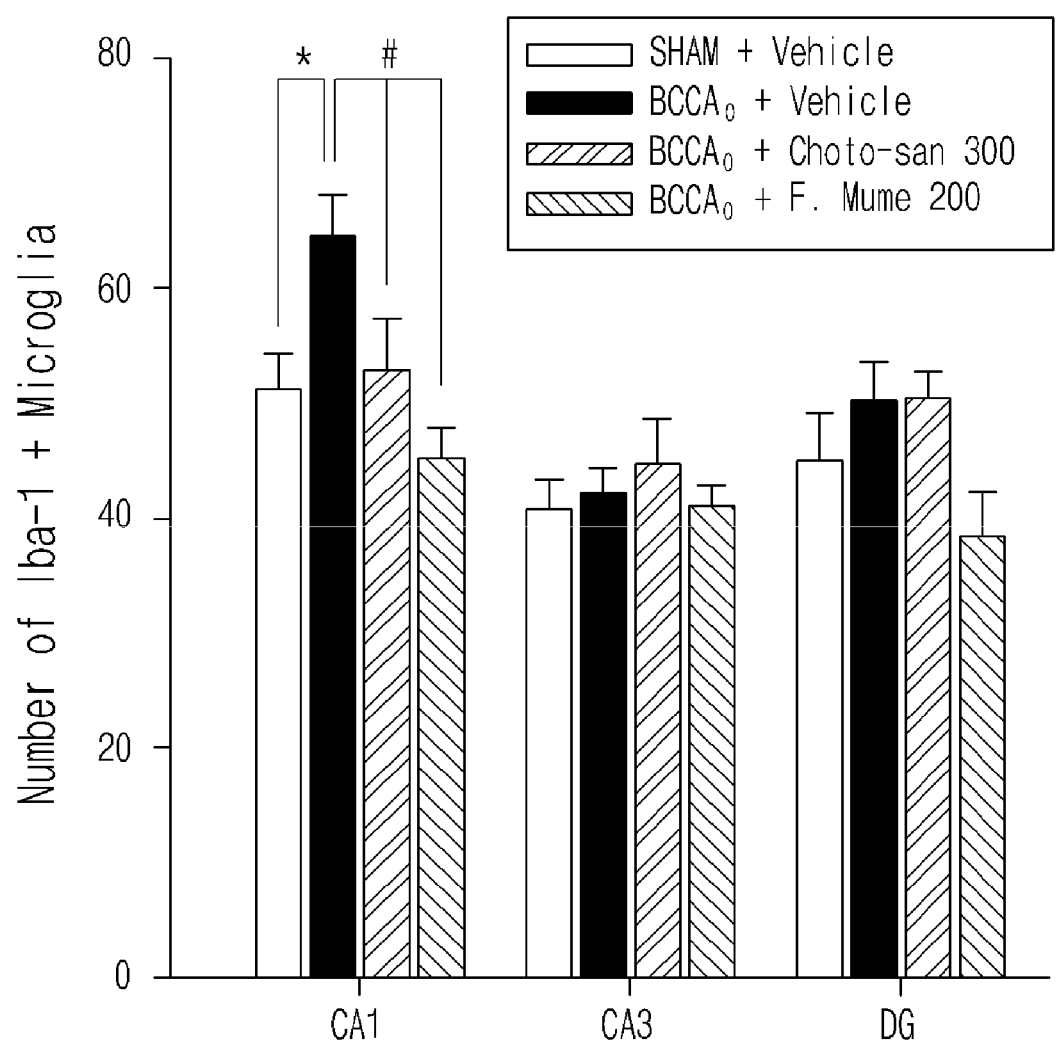

Monoclonal antibody Iba-1 (ionized calcium-binding adaptor molecule) was used to search microglial cells in hippocampus. Iba-1 is expressed in microglial cells and microphases. FIG. 5 illustrates the change in the number of microglial cells in hippocampus according to the administration of the Fructus Mume extract. FIG. 5a illustrates the result of immunohistostaining, and FIG. 5b is a graph illustrating the result of the said immunohistostaining. Compared with the BCCAo group, the vehicle treated group demonstrated significantly high number of microglial cells. The expression level of microglial cells was significantly decreased by the treatment of the Fructus Mume extract of the present invention at the concentration of 200 mg/kg ($p<0.05$).

Figure 6:
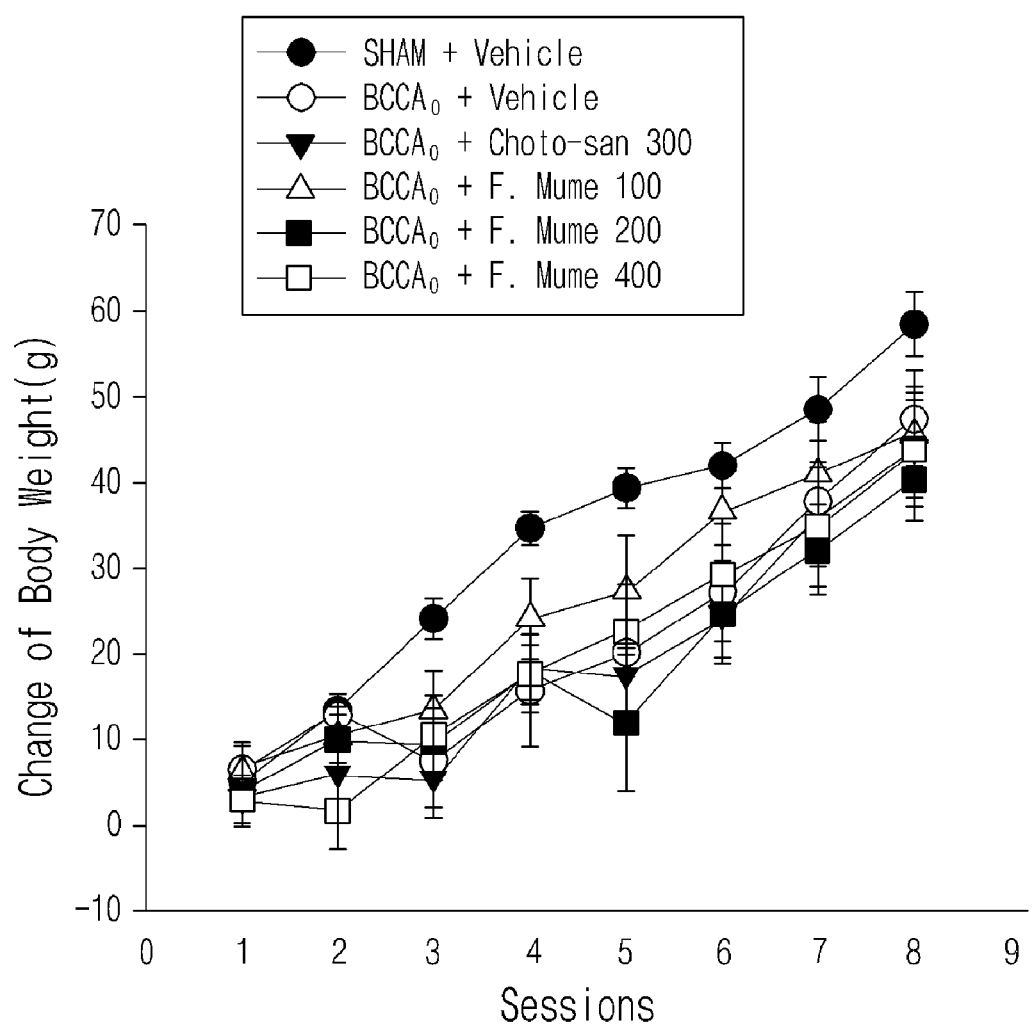
FIG. 6 is a graph illustrating the weight changes over the treatment of the Fructus Mume extract of the present invention.

In a preferred embodiment of the present invention, weight changes of the test animals were observed during the whole experiment period in order to investigate the toxicity of the Fructus Mume extract of the present invention. As a result, body weight of the BCCAo group animal was not increased so much as that of the vehicle treated group, and weight change was hardly observed overall by the treatment of the Fructus Mume extract (FIG. 6). Therefore, it was confirmed that the extract of the present invention has no toxicity, so that it can be effectively used for the prevention or treatment of dementia.

The Fructus Mume extract of the present invention can normalize hippocampal damage efficiently but has no toxicity, so that it can be effectively used for the prevention or treatment of dementia.

The composition for preventing or treating dementia of the present invention can be formulated for oral administration, for example powders, granules, tablets, capsules, suspensions, emulsions, syrups and aerosols, and for parenteral administration, for example external use, suppositories and sterile injections, etc. Solid formulations for oral administration include powders, granules, tablets, capsules, soft capsules, and pills. Liquid formulations for oral administrations are suspensions, solutions, emulsions and syrups, and the above-mentioned formulations can contain various excipients such as wetting agents, sweeteners, aromatics and preservatives in addition to generally used simple diluents such as water and liquid paraffin. For formulations for parenteral administration, powders, granules, tablets, capsules, sterilized suspensions, liquids, water-insoluble excipients, suspensions, emulsions, syrups, suppositories, external use such as aerosols and sterilized injections can be prepared by the conventional method, and preferably skin external pharmaceutical compositions such as creams, gels, patches, sprays, ointments, plasters, lotions, liniments, pastes or cataplasms can be prepared, but not always limited thereto. Water insoluble excipients and suspensions can contain, in addition to the active compound or compounds, propylene glycol, polyethylene glycol, vegetable oil like olive oil, injectable ester like ethylolate, etc. Suppositories can contain, in addition to the active compound or compounds, witepsol, macrogol, tween 61, cacao butter, laurin butter, glycerogelatin, etc.

The composition for preventing or treating dementia of the present invention can additionally include generally used carriers, excipients, disintegrating agents, sweetening agents, lubricants, flavors and diluents. The carriers, excipients and diluents are exemplified by lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate and mineral oil. The disintegrating agents are exemplified by sodium carboxy methyl starch, crospovidone, croscarmellose sodium, alginic acid, calcium carboxymethyl cellulose, sodium carboxymethyl cellulose, chitosan, guar gum, low-substituted hydroxypropyl cellulose, magnesium aluminum silicate, polacrilin potassium, etc.

The composition for preventing or treating dementia of the present invention can additionally include a pharmaceutically acceptable additive, which is exemplified by starch, gelatinized starch, microcrystalline cellulose, lactose, povidone, colloidal silicon dioxide, calcium hydrogen phosphate, lactose, mannitol, taffy, Arabia rubber, pregelatinized starch, corn starch, cellulose powder, hydroxypropyl cellulose, Opadry, sodium carboxy methyl starch, carunauba wax, synthetic aluminum silicate, stearic acid, magnesium stearate, aluminum stearate, calcium stearate, white sugar, dextrose, sorbitol, talc, etc. The pharmaceutically acceptable additive herein is preferably added by 0.1-90 weight part to the pharmaceutical composition.

The composition for preventing or treating dementia of the present invention can include, in addition to the above-mentioned ingredients, one or more effective ingredients having the same or similar function to the Fructus Mume extract. The composition of the present invention can include the Fructus Mume extract by 0.0001-weight %, preferably by 0.001-1 weight % by the total weight of the composition.

The composition for preventing or treating dementia of the present invention can be administered by orally or parenterally and the parenteral administration includes external application to skin, intraperitoneal injection, intrarectal injection, subcutaneous injection, intravenous injection, intramuscular injection or intrathoracic injection.

The present invention also provides a functional health food composition for preventing or alleviating dementia comprising Fructus Mume extract as an active ingredient.

The Fructus Mume extract herein can be prepared by the same manner as described for the preparation of the Fructus Mume extract used as an active ingredient for the composition for preventing or treating dementia.

The said dementia is preferably vascular dementia or Alzheimer's disease, and more preferably vascular dementia, but not always limited thereto.

The Fructus Mume extract of the present invention can be used as a food additive. In that case, the Fructus Mume extract of the present invention can be added as it is or as mixed with other food components according to the conventional method. The mixing ratio of active ingredients can be regulated according to the purpose of use (prevention or alleviation). In general, to produce health food or beverages, the Fructus Mume extract of the present invention is added preferably by 0.2-20 weight %, and more preferably by 0.24-10 weight %. However, if long term administration is required for health and hygiene or regulating health condition, the content can be lower than the above but higher content can be accepted as well since the Fructus Mume extract of the present invention has been proved to be very safe.

The functional health food of the present invention can additionally include various flavors or natural carbohydrates, etc. The natural carbohydrates above can be one of monosaccharides such as glucose and fructose, disaccharides such as maltose and sucrose, polysaccharides such as dextrin and cyclodextrin, and glucose alcohols such as xylytole, sorbitol and erythritol. Besides, natural sweetening agents such as thaumatin and stevia extract, and synthetic sweetening agents such as saccharin and aspartame can be included as a sweetening agent. The content of the natural carbohydrate is preferably 0.01-0.04 weight part and more preferably 0.02-0.03 weight part in 100 weight part of the functional health food of the present invention.

The functional health food herein is not limited. For example, the Fructus Mume extract of the present invention can be added to drinks, meat, sausages, bread, biscuits, tteok (rice cake), chocolates, candies, snacks, cookies, pizza, ramyuns, flour products, gums, dairy products including ice cream, soups, beverages, alcohol drinks and vitamin complex, etc, and in wide sense, almost every food applicable in the production of health food can be included.

In addition to the ingredients mentioned above, the functional health food of the present invention can include in a variety of nutrients, vitamins, minerals, flavors, coloring agents, pectic acid and its salts, alginic acid and its salts, organic acid, protective colloidal viscosifiers, pH regulators, stabilizers, antiseptics, glycerin, alcohols, carbonators which used to be added to soda, etc. The functional health food of the present invention can also include natural fruit juice, fruit beverages and/or fruit flesh addable to vegetable beverages. All the mentioned ingredients can be added singly or together. The mixing ratio of those ingredients does not matter in fact, but in general, each can be added by 0.01-0.1 weight part per 100 weight part of the functional health food of the present invention.

The present invention further provides a method for the treatment of dementia containing the step of administering a pharmaceutically effective dose of Fructus Mume extract to a subject having dementia.

In addition, the present invention provides a method for the prevention of dementia containing the step of administering a pharmaceutically effective dose of Fructus Mume extract to a subject.

The said dementia is preferably vascular dementia or Alzheimer's disease.

The subject herein can be any animal including human.

The Fructus Mume extract can additionally include one or more effective ingredients having the same or similar function to the Fructus Mume extract.

The administration can be performed by oral administration or parental administration including subcutaneous injection, intravenous injection, or intramuscular injection. The Fructus Mume extract of the present invention can be used in general forms of pharmaceutical formulation.

The dosage units can contain, for example, 1, 2, 3 or individual doses or ½, ⅓ or ¼ of an individual dose. An individual dose preferably contains the amount of active compound which is administered in one application and which usually corresponds to a whole, ½, ⅓ or ¼ of a daily dose. The effective dosage is 0.0001-10 g/kg per day, and preferably 0.0001-5 g/kg per day, and administration frequency is preferably 1-6 times a day.

Practical and presently preferred embodiments of the present invention are illustrative as shown in the following Examples, Experimental Examples and Manufacturing Examples.

However, it will be appreciated that those skilled in the art, on consideration of this disclosure, may make modifications and improvements within the spirit and scope of the present invention.

Example 1: Preparation of Fructus Mume Extract

The Fructus Mume used in this example was purchased from Kwangmyungdang (Ulsan, Korea) and external morphology was checked by Herbal Quality Control Team, Korea Institute of Oriental Medicine before used in the experiment. The dried Fructus Mume (2 kg) was placed in ultrasonification/heat combined extractor (OM30-EP, SONIMEDI), to which 8 l of distilled water was added. Extraction was performed at 95° C. for 120 minutes. The extracted solution was loaded in Exdryer (SONIMEDI), followed by drying at 80° C., −95 kPa or under, for 48 hours to give Fructus Mume extract (yield: 16.225%).

Example 2: Construction of Vascular Dementia Animal Model and Oral Administration of Drug (In Vivo)

<2-1> Construction of Vascular Dementia Animal Model

To investigate the effect of the Fructus Mume extract of the present invention on the inhibition of vascular dementia progress, the following experiment was performed. The test animals used in this example were Wister rats at 12 weeks in the weight of 350-400 g. After obtaining the test animals, the appearance was checked by visual examination. The animals were then adapted for 7 days. After observing any general symptoms, only healthy animals were selected, which were grouped randomly but according to the weight. The environmental conditions for the adaptation period and the experiment period were as follows; temperature: 23±3° C., relative humidity: 50±10%, air circulation: 12-16 times per hour, light/dark cycle: 12/12 hour (turn on at 7:00 and turn off at 19:00), illumination intensity: 150-300 Lx. All the tools were sterilized. Water and solid feeds (RMI nutrition, USA) were provided freely for 24 hours. To construct vascular dementia animal model, chronic cerebral hypoperfusion was induced by bilateral common carotid artery occulusion (2VO, referred as "BCCAo" hereinafter) (Wakita et al., 1994). Briefly, the animal was anesthetized with 4% isoflurane and the anesthesia was maintained by 1.5% isoflurane during the operation. Central neck was incised to expose bilateral common carotid artery carefully not to give any damage on vagus nerve. Ligation was performed twice with #3 silk.

<2-2> Oral Administration of Drug to Vascular Dementia Animal Model

The experimental groups were prepared as follows: Wistar rats were orally administered with Fructus Mume extract after the BCCAo operation. Total 6 groups were prepared and each group was composed of 16 rats. According to the result of preliminary experiment, approximately 40% of rats had vision disorder. Therefore, the animals were divided into blind group and non-blind group by using shuttle box one week before behavioral analysis (water maze test). The rats in the blind group were orally administered with the extract for 42 days, while the rats in the non-blind group were finished with memory test and then orally administered with the extract for 42 days.

TABLE 1

| Group | Cognitive function test (number) | Weight change and neurobiological test (number) |
| --- | --- | --- |
| Vehicle treated group | 8 | 16 |
| Brain damaged group (BCCAo) | 8 | 16 |
| BCCAo + Chotosan 300 mg/kg | 8 | 15 |
| BCCAo + Fructus Mume 100 mg/kg | 8 | 14 |
| BCCAo + Fructus Mume 200 mg/kg | 7 | 14 |
| BCCAo + Fructus Mume 400 mg/kg | 8 | 15 |

Table 1 illustrates the cognitive function test. The concentration of the Fructus Mume extract of the present invention was differently prepared as low concentration (100 mg/kg), medium concentration (200 mg/kg), and high concentration (400 mg/kg). Experiment was designed with total 6 groups including the control group treated with Chotosan (300 mg/kg), the vehicle treated group, and the experimental groups.

Example 3: Spatial Recognition Test with Vascular Dementia Animal Model (In Vivo)

Following experiment was performed to investigate the effect of the Fructus Mume extract of the present invention on the vascular dementia animal model via behavior test. Behavior test was performed by water maze test. Particularly, screen walls were set up on every sides of the water maze to prevent light coming through and the circular water tank was filled with water (diameter: 183 cm, height: 58 cm) at the temperature of 26±2° C. up to 2 cm above the marked platform. Pigment was added to the water to make the water not transparent. To give clues for the rat to search the marked platform, labels were attached on specific sites on the screen wall. The marked platform (diameter: 12 cm, height: 33.5 cm) was set in a designated area of the water tank. This was designed for the rat to swim to the marked platform to survive. After entering the water, the time, the distance, and the speed for the rat to swim to the marked platform were measured, which became markers for memory. Training trial (ability to find and swim to the marked platform after entering the water) was performed after administering the rat with the Fructus Mume extract of Example 1 for 3 weeks. The movement of the rat was measured starting with the training, leading to the measurement of the time and the distance of swimming. The time and the distance were compared every day among the groups. As the time and the distance shortened fast, it was assumed that learning effect was greater. Training trial was performed for 8 days, once a day, 8 times in total, every morning (9:00 am). Spatial recognition ability was evaluated over the long-term oral treatment of the Fructus Mume extract of Example 1. Cognitive performance (spatial recognition ability) was evaluated after the training, 4 times a day for 8 days. Spatial recognition ability test was performed on day 4 and day 8 after the training trail. One week later, cued training was performed (6 times a day).

From the result of spatial memory test performed in water maze, it was confirmed that hippocampal dependent learning and memory defects were observed in the Fructus Mume extract treated group, compared with the BCCAo group (FIG. 1). The vehicle treated group animals carried out spatial memory task in water maze well, compared with the BCCAo group animals. In the group treated with 200 mg/kg of the Fructus Mume extract of Example 1, the animals demonstrated as good spatial memory learning ability as the control group. From the result of statistical evaluation, it was confirmed that there was a difference among the groups ($F(5,53)=8.26$, $p=0.000$) and as training trail repeated, the speed to find the hidden platform increased ($F(3,159)=98.48$, $p=0.000$). According to the post hoc performed to analyze the difference among the groups, the animal administered with 200 mg/kg of the Fructus Mume extract demonstrated excellent spatial memory learning ability, compared with the animals of the BCCAo group ($p=0.027$). Therefore, the Fructus Mume extract of the present invention was confirmed to be able to normalize spatial memory ability efficiently and be used effectively for the prevention or treatment of dementia.

From the results of two probe trails, it was confirmed that the BCCAo group hardly remembered the location of the platform ($F(5,53)=7.05$, $p=0.000$), compared with the vehicle treated group (FIG. 2). Probe trials were performed 4 days and 8 days after training. As a result, the animals of the BCCAo group and the group treated with 200 mg/kg of the Fructus Mume extract swam significantly less than the animals of the vehicle treated group in the area 5 times as big as the platform ($p=0.014$, first probe trial). Therefore, it was confirmed that the Fructus Mume extract of the present invention increased memory ability of the animals.

Figure 3:
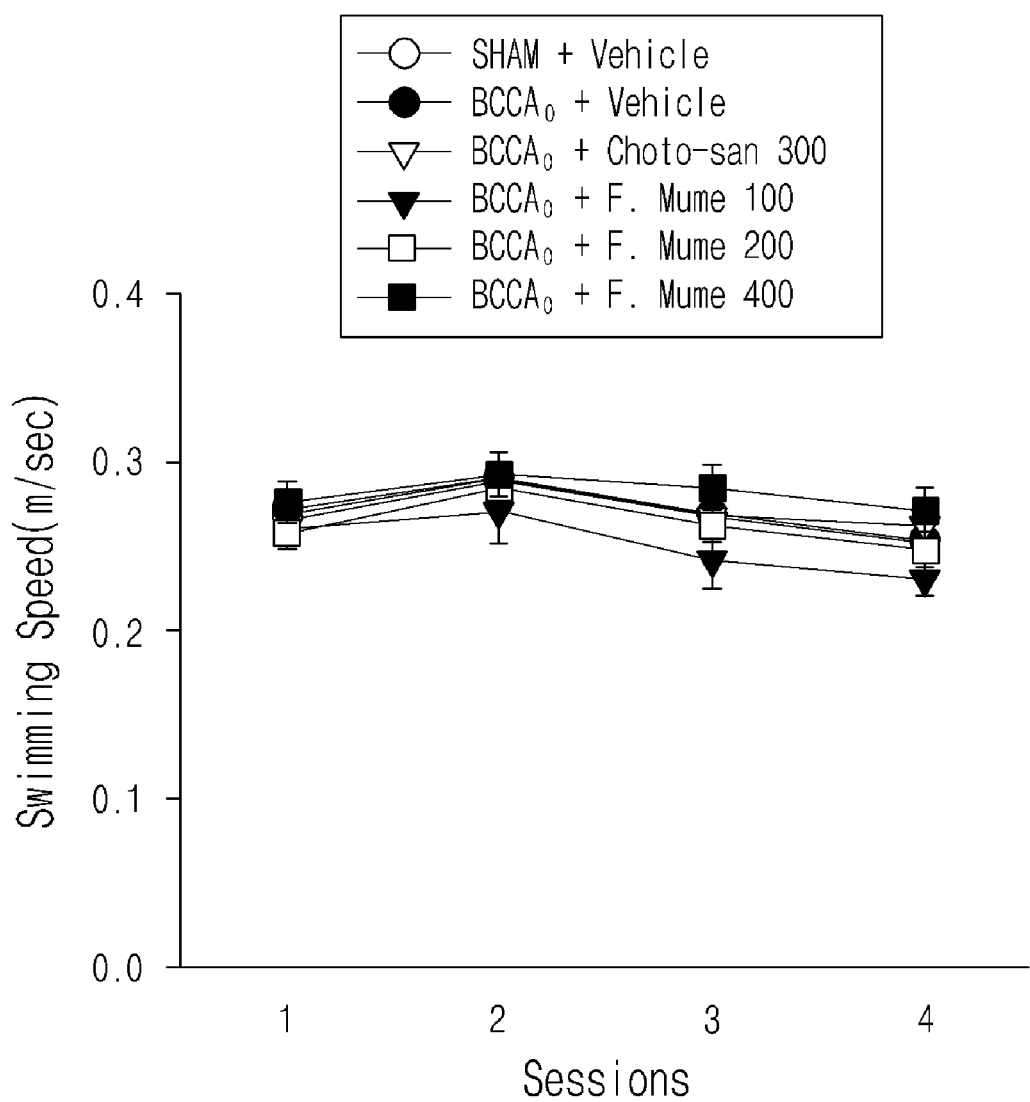
FIG. 3 is a graph illustrating swimming speed (m/sec) over trail sessions, indicating that there is no exercise disorder found by brain damage.

The average swim speed during the trial in the water maze was not much different among the groups (FIG. 3), which means there was no exercise disorder in any group.

TABLE 2

| Group | Time (sec) |
|---|---|
| Vehicle treated group | 10.80 |
| Brain damaged group (BCCAo) | 16.13 |
| BCCAo + Chotosan 300 mg/kg | 26.15 |
| BCCAo + Fructus Mume 100 mg/kg | 21.66 |
| BCCAo + Fructus Mume 200 mg/kg | 9.84 |
| BCCAo + Fructus Mume 400 mg/kg | 21.50 |

Table 2 illustrates the result of cued training. The platform had dark color and floated on the surface of water so that the rat could see easily. If a rat showed disorder in that test, it must have been exercise disorder or striatum disorder. Some differences among the groups were observed during the 6 cued training trials. The group treated with 200 mg/kg of the Fructus Mume extract showed similar performance to the vehicle treated group.

Example 4: Neurobiological Index Test with Vascular Dementia Animal Model (In Vivo)

Upon completion of the experiment, hippocampus was quick-frozen, which was stored in a cryogenic refrigerator (−80° C.) for the duration of the test. The quick-frozen brain tissue of the rat was melted on ice, to which cold protein lysis buffer (1 M Tris [pH7.5], 0.5 M EDTA, 1 M KCl, Glycerol 100%, 100 nM Dithiothreitol, proteinase inhibitor) was added, leading to the homogenization for 8 minutes. The tissue proceeded to ultracentrifugation for 1 hour (14,000 rpm, 4° C., vacuum) and then the supernatant formed in the top of the test tube was collected. Each protein was quantified by Bradford method, followed by protein stabilization with sample buffer. Each protein sample proceeded to SDS-polyacrylamide gel electrophoresis at 100 V. The obtained protein band was transferred onto PVDF (polyvinylidene fluoride) membrane by using the transfer unit for one hour at 100 V, 400 mA. Then, the membrane was washed with TBST once, followed by blocking with 5% skim milk (1 hour, at room temperature). The membrane was washed again with TBST three times (10 min/each time) and then reacted with ERK primary antibody (p44/42 mapkinase antibody (cell signaling, #9102)), pERK primary antibody (phospho-p44/42 MAPK antibody (cell signaling, #9101S)), ChAT primary antibody (Chemicon, lot0512017589), NF-kappa B p65 primary antibody (Upstate Biotechnology), IκBα primary antibody, and β-actin primary antibody (sigma) diluted in 5% skim milk (1:1000) at 4° C. for overnight. On the next day, the membrane was washed again with TBST three times (10 min/each time) and then reacted with anti-rabbit IgG secondary antibody (Amersham) diluted in 5% skim milk (1:5000) at room temperature for 1 hour. The membrane was washed again with TBST three times (10 min/each time), and reacted with ECL solution, followed by the development on film.

FIG. 4 illustrates the changes of ERK (extracellular signal-regulated kinase) phosphorylation, ChAT (choline acetyltransferase, IκB (Inhibitor of κB), NF-kappa B (nuclear factor kappa-light-chain-enhancer of activated B cells) according to the treatment of the Fructus Mume extract of the present invention. FIG. 4a illustrates the result of western blotting. FIG. 4a illustrates the result of Western blotting and FIG. 4b is a graph illustrating the result presenting the normalization of hippocampal damage (normalizing ERK phosphorylation and increasing ChAT) by the administration of the Fructus Mume extract of the present invention. FIG. 4c illustrates the result of Western blotting and FIG. 4d is a graph illustrating the result presenting the normalization of hippocampal damage (normalizing NF-kappa B) by the administration of the Fructus Mume extract of the present invention. The BCCAo group animals demonstrated similar ERK level but higher ERK phosphorylation, compared with the vehicle treated group animals. The treatment of the Fructus Mume extract reduced ERK phosphorylation level significantly (p<0.05). Hippocampal ChAT (choline acetyltransferase, the enzyme used for the generation of acetylcholine) was reduced in the BCCAo group animals, compared with the vehicle treated group, and the reduced ChAT level was normalized by the administration of the Fructus Mume extract. NF-Kappa B level was also normalized by the treatment of the Fructus Mume extract.

Therefore, it was confirmed that the Fructus Mume extract of the present invention can be effectively used for the prevention or treatment of dementia since it could normalize hippocampal damage efficiently.

Example 5: Histological Index Test with Vascular Dementia Animal Model (In Vivo)

The rat used for histological index test was anesthetized with the mixture of ketamin HCl (30 mg/kg) and xylazine (2.5 mg/kg), followed by perfusion with 4% paraformaldehyde (PFA) in 0.01 M PBS. The brain was taken and post-fixed in 4% PFA for 2 days, which was then cryoprotected in PBS containing 30% sucrose for 48 hours (protecting tissues from cold). The brain was frozen in powdered dry-ice and stored at −70° C. until use. The perfused brain tissues were sliced into 40 μm thick sections by using microtome, which were stored in 4° C. PBS. To screen microglial cells in hippocampus, monoclonal antibody Iba-1 (ionized calcium-binding adaptor molecule) was used. Iba-1 is expressed in microglial cells and microphases. For the Iba-1 immune response, free floating section resistant peroxidase was quenched through incubation in 3% $H_2O_2$/10% MeOH PBS for 30 minutes. Then, the tissues were incubated in 0.3% Triton-X 100 (PBS-T-S) PBS containing 10% serum at room temperature for 1 hour. The tissues were incubated again in 3% PBS-T-S solution in the presence of Iba-1 antibody at 4° C. for 12 hours. Then, the tissues were incubated with horse anti-mouse antibody (Vector: 1:200) and Extravidin peroxidase conjugate (Sigma Aldrich; 1:1000) for 1 hour, respectively. Lastly, the tissues were reacted with Vector SG substrate kit (Sigma Aldrich) for peroxidase, which were placed on the slide coated with synthetic resin, followed by drying for a week. The dried tissues on the slice were covered with the slide cover by using permount reagent. The reacted microglia was quantified by statistic analysis. As a result, microglia was detected in hippocampus among the 6 brain parts of each animal by using Iba-1 antibody.

FIG. 5 illustrates the change in the number of microglial cells in hippocampus according to the administration of the Fructus Mume extract. FIG. 5a illustrates the result of immunohistostaining, and FIG. 5b is a graph illustrating the result of the said immunohistostaining. Compared with the BCCAo group, the vehicle treated group demonstrated significantly high number of microglial cells. The expression level of microglial cells was significantly decreased by the treatment of the Fructus Mume extract of the present invention at the concentration of 200 mg/kg (p<0.05).

Therefore, it was confirmed that the Fructus Mume extract of the present invention can be effectively used for the prevention or treatment of dementia since it could normalize hippocampal damage efficiently.

Example 6: Toxicity Test with Fructus Mume Extract

To investigate toxicity of the Fructus Mume extract of the present invention, weight changes were observed for the duration of the experiment.

FIG. 6 illustrates the weight changes over the treatment of the Fructus Mume extract. Body weight of the BCCAo group animal was not increased as much as that of the vehicle treated group, and weight change was hardly observed overall by the treatment of the Fructus Mume extract. Therefore, it was confirmed that the extract of the present invention has no toxicity, so that it can be effectively used for the prevention or treatment of dementia.

The Manufacturing Examples for the composition of the present invention are described hereinafter.

Manufacturing Example 1: Preparation of Pharmaceutical Formulations

1. Preparation of Powders

| | |
|---|---|
| Fructus Mume ultrasonification/heat combined extract | 2 g |
| Lactose | 1 g |

Powders were prepared by mixing all the above components, which were filled in airtight packs according to the conventional method for preparing powders.

2. Preparation of Tablets

| | |
|---|---|
| Fructus Mume ultrasonification/heat combined extract | 100 mg |
| Corn starch | 100 mg |
| Lactose | 100 mg |
| Magnesium stearate | 2 mg |

Tablets were prepared by mixing all the above components by the conventional method for preparing tablets.

3. Preparation of Capsules

| | |
|---|---|
| Fructus Mume ultrasonification/heat combined extract | 100 mg |
| Corn starch | 100 mg |
| Lactose | 100 mg |
| Magnesium stearate | 2 mg |

Capsules were prepared by mixing all the above components, which were filled in gelatin capsules according to the conventional method for preparing capsules.

4. Preparation of Pills

| | |
|---|---|
| Fructus Mume ultrasonification/ heat combined extract | 1 g |
| Lactose | 1.5 g |
| Glycerin | 1 g |
| Xylitol | 0.5 g |

Pills were prepared by mixing all the above components according to the conventional method for preparing pills. Each pill contained 4 g of the mixture.

5. Preparation of Granules

| | |
|---|---|
| Fructus Mume ultrasonification/ heat combined extract | 150 mg |
| Soybean extract | 50 mg |
| Glucose | 200 mg |
| Starch | 600 mg |

All the above components were mixed, to which 100 mg of 30% ethanol was added. The mixture was dried at 60° C. and the prepared granules were filled in packs.

Manufacturing Example 2: Preparation of Food

1. Preparation of Flour Food 0.5-5.0 weight part of the Fructus Mume ultrasonification/heat combined extract of the present invention was added to the flour. Health enhancing food such as bread, cake, cookies, crackers and noodles was prepared with the flour mixture according to the conventional method.

2. Preparation of Soups and Gravies 0.1-5.0 weight part of the Fructus Mume ultrasonification/heat combined extract of the present invention was added to soups and gravies. Health enhancing meat products, soups and gravies were prepared with this mixture by the conventional method.

3. Preparation of Ground Beef

Health enhancing ground beef was prepared by mixing 10 weight part of the Fructus Mume ultrasonification/heat combined extract of the present invention with ground beef according to the conventional method.

4. Preparation of Dairy Products 5-10 weight part of the Fructus Mume ultrasonification/heat combined extract of the present invention was added to milk. Health enhancing dairy products such as butter and ice cream were prepared with the milk mixture according to the conventional method.

5. Preparation of Sun-Sik

Brown rice, barley, glutinous rice and Yulmu (Job's tears) were gelatinized according to the conventional method, dried and pulverized to obtain 60-mesh powders.

Black soybean, black sesame and wild sesame were steamed and dried according to the conventional method and pulverized to obtain 60-mesh powders.

The Fructus Mume ultrasonification/heat combined extract of the present invention was concentrated under reduced pressure, spray-dried and pulverized to obtain 60-mesh dry powders.

Sun-Sik was prepared by mixing the dry powders of the grains, seeds and the Fructus Mume ultrasonification/heat combined extract of the present invention according to the below ratio.

Grains (brown rice: 30 weight part, Yulmu: 15 weight part, barley: 20 weight part), Seeds (wild sesame: 7 weight part, black soybean: 8 weight part, black sesame: 7 weight part), Dry powders of the Fructus Mume ultrasonification/heat combined extract of the present invention (3 weight part),

*Ganoderma lucidum* (0.5 weight part),

*Rehmannia glutinosa* (0.5 weight part)

Manufacturing Example 3: Preparation of Beverages

1. Preparation of Health Beverages

The Fructus Mume ultrasonification/heat combined extract of the present invention (5 g) was mixed with liquid fructose (0.5 weight %), oligosaccharide (2 weight %), sugar (2 weight %), salt (0.5 weight %), and water (75 weight %). After mixing completely, the mixture was sterilized instantly and filled small containers such as glass bottles, pet bottles, etc, to prepare health beverages.

2. Preparation of Vegetable Juice

Health enhancing vegetable juice was prepared by adding 5 g of the Fructus Mume ultrasonification/heat combined extract of the present invention to 1,000 ml of tomato or carrot juice according to the conventional method.

3. Preparation of Fruit Juice

Health enhancing fruit juice was prepared by adding 1 g of the Fructus Mume ultrasonification/heat combined extract of the present invention to 1,000 ml of apple or grape juice according to the conventional method.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A method for the treatment of dementia comprising:
   administering a composition consisting essentially of an effective amount of an extract of Fructus Mume to a subject having dementia,
   wherein the extract of Fructus mume is a water extract, $C_1$-$C_4$ lower alcohol extract, or a water and $C_1$-$C_4$ lower alcohol extract.

2. The method according to claim 1, wherein the lower alcohol is ethanol or methanol.

3. The method according to claim 1, wherein the extract of Fructus Mume is extracted by a combination of ultrasonification and heat extraction.

4. The method according to claim 1, wherein the dementia is vascular dementia or Alzheimer's disease.

* * * * *